(12) United States Patent
Collins et al.

(10) Patent No.: US 7,070,612 B1
(45) Date of Patent: Jul. 4, 2006

(54) SYSTEM AND METHOD FOR BRINGING HYPOTHERMIA RAPIDLY ONBOARD

(75) Inventors: Kenneth A. Collins, Mission Viejo, CA (US); William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 11/108,281

(22) Filed: Apr. 18, 2005

Related U.S. Application Data

(63) Continuation-in-part of application No. 11/064,187, filed on Feb. 23, 2005.

(51) Int. Cl.
*A61F 7/00* (2006.01)

(52) U.S. Cl. .................. 607/105; 607/106; 607/108

(58) Field of Classification Search ........ 607/104–114, 607/96
See application file for complete search history.

(56) References Cited

U.S. PATENT DOCUMENTS

| | | | |
|---|---|---|---|
| 6,581,403 B1* | 6/2003 | Whitebook et al. | 62/434 |
| 6,673,098 B1* | 1/2004 | Machold et al. | 607/96 |
| 6,878,156 B1* | 4/2005 | Noda | 607/106 |
| 7,004,960 B1* | 2/2006 | Daoud | 607/105 |
| 2004/0162520 A1* | 8/2004 | Noda et al. | 604/113 |

* cited by examiner

*Primary Examiner*—Roy D. Gibson
(74) *Attorney, Agent, or Firm*—John L. Rogitz

(57) ABSTRACT

An intravenous heat exchange catheter and/or an external cooling pad/bladder can be used to maintain hypothermia in, e.g., a cardiac arrest patient, but to accelerate the cooling process the patient first can be infused with cold saline before the opportunity arises to connect the catheter or pad to the patient.

19 Claims, 9 Drawing Sheets

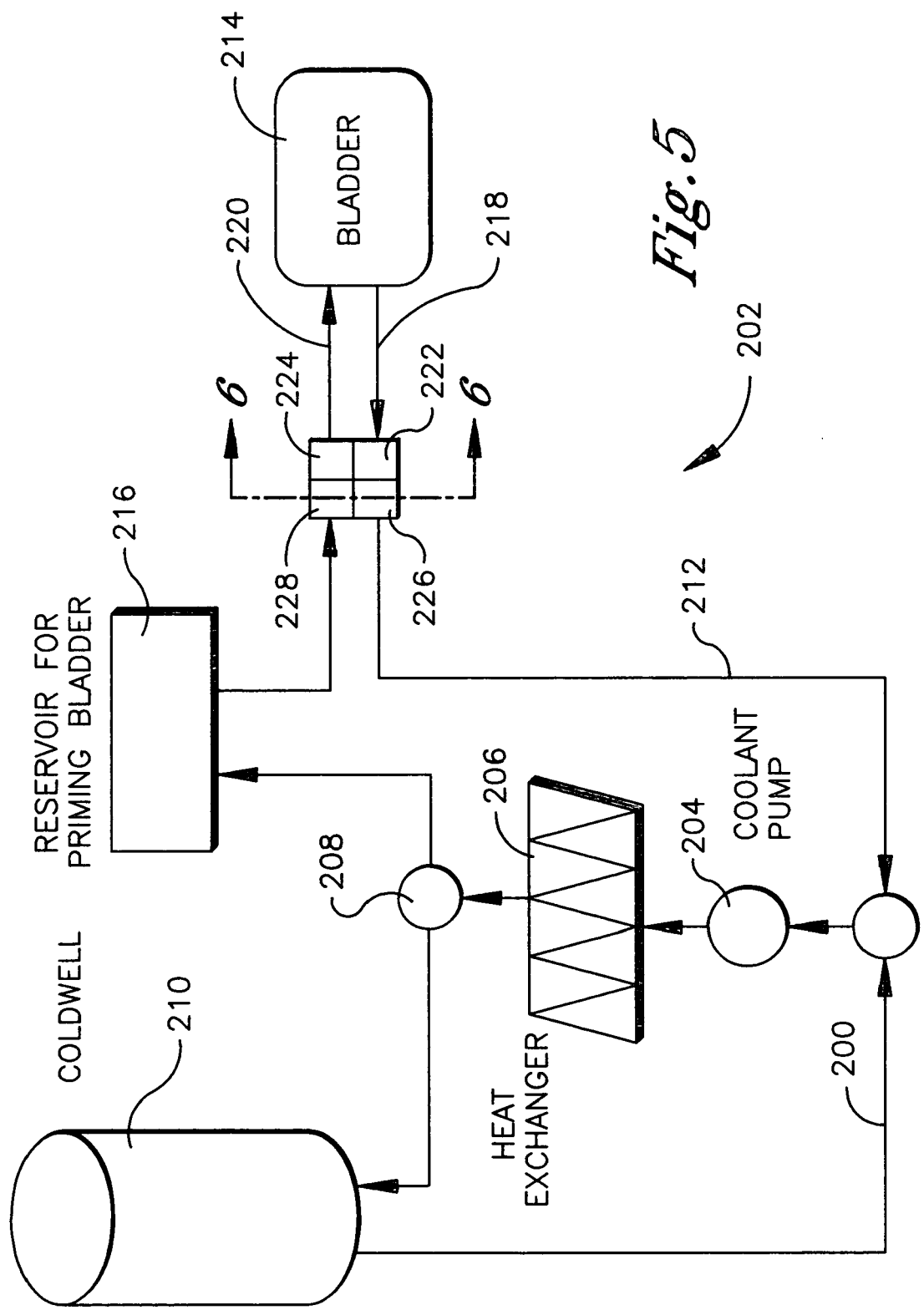

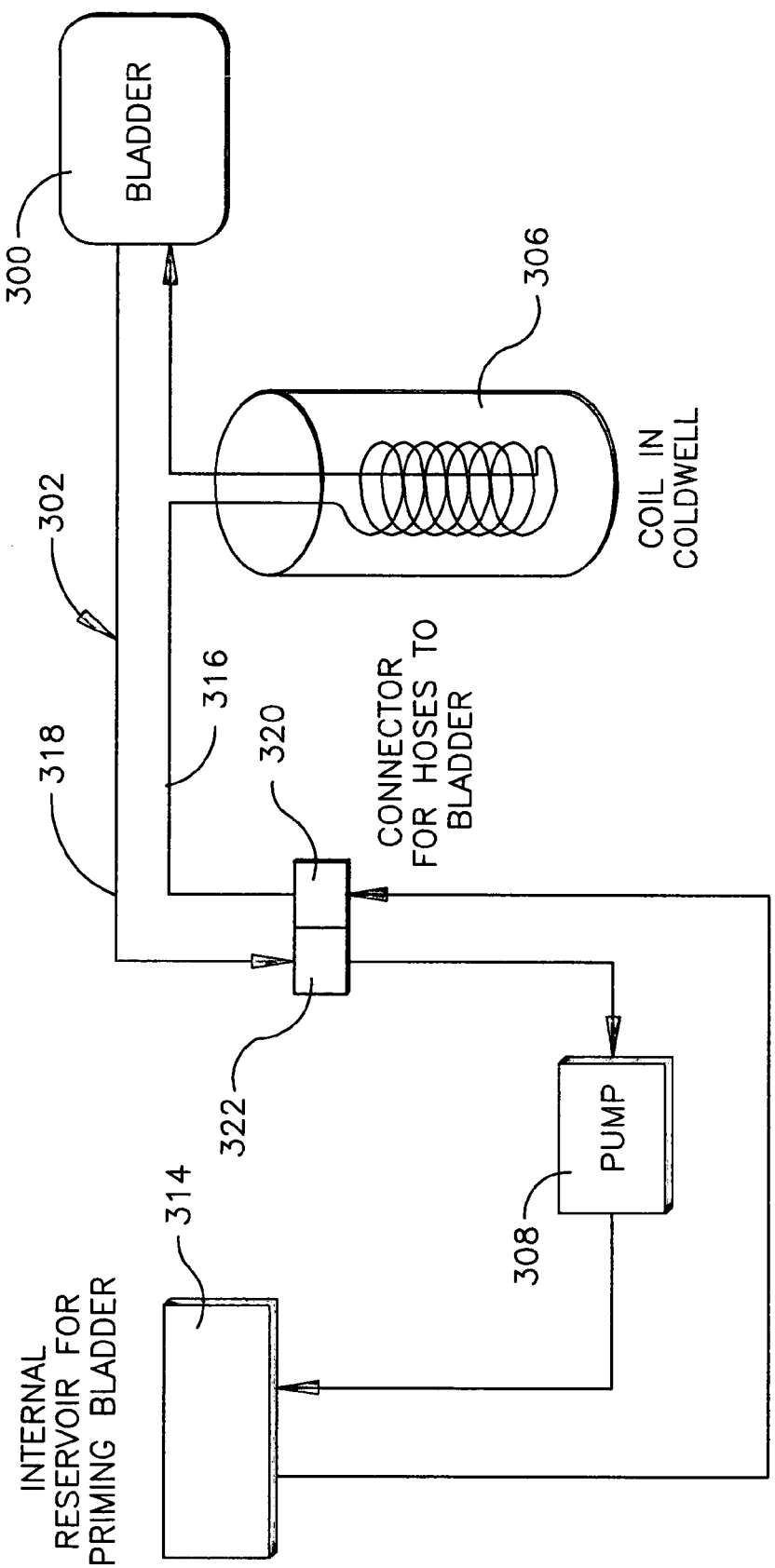

SYSTEM AND METHOD FOR BRINGING HYPOTHERMIA RAPIDLY ONBOARD

This is a continuation-in-part of U.S. patent application Ser. No. 11/064,187, filed Feb. 23, 2005, from which priority is claimed.

FIELD OF THE INVENTION

The present invention relates generally to therapeutic hypothermia.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

Surface cooling may be less optimally used. For example, externally applied cooling pads are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

Regardless of the modality of cooling, it is believed that the sooner a patient is cooled after ischemic insult, the better the therapy. The present invention recognizes that many patients will have their first encounter with health care personnel in ambulances, prior to being afforded the opportunity for critical care such as controlled maintenance of hypothermia. Thus, it would be advantageous, as understood herein, to provide a means to bring cooling on board to patients as soon as possible.

SUMMARY OF THE INVENTION

A system for controlling patient temperature includes a closed loop heat exchange catheter configured for placement in the circulatory system of a patient to exchange heat with the blood of the patient. The system also includes a source of cold fluid, with the cold fluid being colder than normal body temperature and infusable from the source into the patient without using the catheter.

The catheter may be configured for percutaneous advancement into the central venous system of the patient. The catheter can carry coolant that is not infused into the bloodstream of the patient.

In another aspect, a method for treating a patient using hypothermia includes injecting cold saline into the venous system of the patient while the patient is located in an ambulance or in an emergency room of a hospital. Then subsequently hypothermia is maintained in the patient using an external heat exchange pad or an intravascular heat exchange catheter while the patient is in an operating room of a hospital or an intensive care unit of a hospital.

In yet another aspect, a method for treating a patient includes infusing into the patient's venous system a cold fluid having a temperature lower than a temperature of the patient to cause the fluid to mix with the blood of the patient and thereby to cool the patient. The method also includes engaging a cooling apparatus with the patient to maintain a desired hypothermic condition in the patient.

In additional embodiments, a system for controlling patient temperature includes a closed loop heat exchange catheter configured for placement in the circulatory system of a patient to exchange heat with the blood of the patient, and an external heat exchange bladder configured for exchanging heat with the skin of a patient. The system also includes a heat exchange system in a single housing and engageable with both the catheter and the bladder.

In non-limiting implementations of this last embodiment, the housing can include a sensor which detects when the heat exchange system is connected to the bladder, and potentially to the catheter as well, to provide a signal to a controller in the housing. Additionally, a controller may be in the housing and receive a patient temperature signal from a BTT sensor. Further, an IV bag can be supported on the housing for infusing cold saline directly into the bloodstream of a patient.

Continuing to summarize non-limiting implementations, the heat exchange system may include a coolant loop configured for exchanging heat with a working fluid loop associated with the catheter. The coolant loop may also be configured for direct fluid communication with the bladder. Or, the heat exchange system can include a coolant loop having a coldwell, with the catheter being associated with a catheter working fluid loop including a catheter coil disposable in the coldwell and with the bladder being associated with a bladder working fluid loop including a bladder coil disposable in the coldwell. Both working fluid loops may be associated with respective pumps. The heat exchange system may also include an internal reservoir for priming the bladder, and may control both the catheter and bladder simultaneously. The heat exchange system can include a refrigerant loop including a compressor and one or more heat exchangers communicating with the compressor.

In another aspect, a heat exchange system includes a coolant loop, at least a first working fluid loop in thermal communication with the coolant loop and an intravascular heat exchange catheter associated with the first working fluid loop such that working fluid circulates through the heat exchange catheter without entering the patient's bloodstream when the catheter is positioned in the bloodstream. At least one external heat exchange member is configured for placement against a patient's skin to heat or cool the skin. The external heat exchange member is configured for heat transfer using the coolant loop.

In another aspect, a method for patient temperature control includes providing a heat exchange system, and engaging an intravascular heat exchange catheter with the system and with a patient to exchange heat with the patient. The method also includes engaging at least one bladder with the system and placing the bladder against the patient's skin to exchange heat with the patient.

In other aspects, a patient temperature control system includes at least one bladder through which working fluid can flow. The bladder is positionable against the skin of a patient, and a skin conditioning hydrogel can be disposed between the bladder and the skin.

In another aspect, a patient temperature control system includes at least one bladder through which working fluid can flow, with the bladder being configured as the front of a garment and having a trunk portion and two opposed limb portions that can drape over the patient.

In another aspect, a patient temperature control system includes at least one bladder through which working fluid can flow. The surface of the bladder facing away from a patient when the bladder is positioned against the skin of the patient is backed by a foam that conforms to pressure caused by the weight of the patient.

The details of the present invention, both as to its structure and operation, can best be understood in reference to the accompanying drawings, in which like reference numerals refer to like parts, and in which:

BRIEF DESCRIPTION OF THE DRAWINGS

FIG. 5 is a schematic diagram of an alternate system;

FIG. 8 is a schematic diagram of an alternate system.

DETAILED DESCRIPTION OF THE PREFERRED EMBODIMENT

Figure 1:
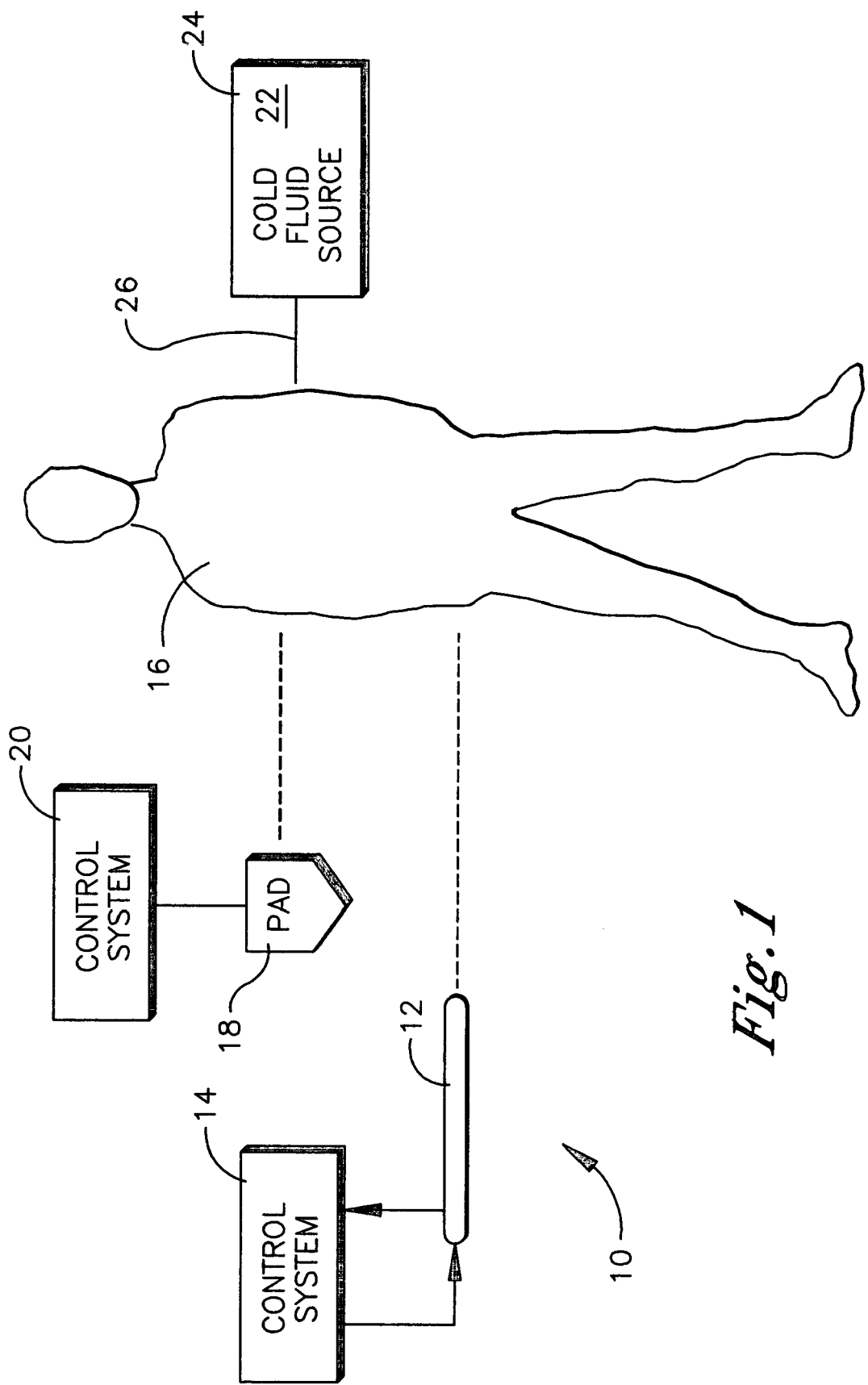
FIG. 1 is a schematic diagram showing two modalities of controlled hypothermia maintenance in a patient, along with an apparatus for quickly reducing patient temperature.

Referring initially to FIG. 1, a system is shown, generally designated 10, that includes a heat exchange catheter 12 that is in fluid communication with a catheter temperature control system 14.

In accordance with present principles, the system 10 can be used to induce therapeutic hypothermia in a patient 16 using a catheter in which coolant circulates in a closed loop, such that no coolant enters the body. While certain preferred catheters are disclosed below, it is to be understood that other catheters can be used in accordance with present principles, including, without limitation, any of the catheters disclosed in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by a pad controller 20 in accordance with principles set forth in the external pad patents to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia.

To cool the patient while awaiting engagement of the catheter 12 and/or pad 18 with the patient, cold fluid 22 in a cold fluid source 24 may be injected into the patient and in particular into the patient's venous system through a pathway 26. Without limitation, the pathway 26 may an IV line, the source 24 may be an IV bag, and the fluid 22 may be chilled saline, e.g., saline at the freezing point or slightly warmer. Or, the source may be a syringe, and the saline can be injected directly into the bloodstream of the patient.

Figure 2:
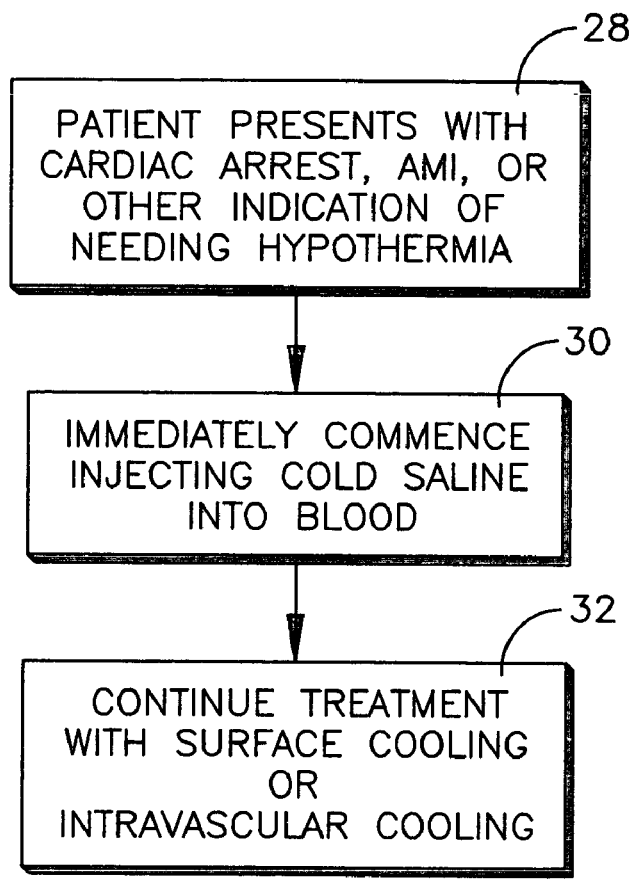
FIG. 2 is a flow chart of logic.

Now referring to FIG. 2, at block 28 the patient presents with symptoms indicating that the application of hypothermia is appropriate. For instance, the patient may have cardiac arrest, and may be resuscitated. Or, the patient may present with myocardial infarction or stroke or other malady.

At block 30, cold saline 22 is immediately (in the case of cardiac arrest patients, immediately after resuscitation) injected into the patient's bloodstream, preferably at a venous site, using the source 24. This can occur in, e.g., an ambulance on the way to the hospital for further temperature management, and/or in the hospital emergency room. Hypothermia treatment including the establishment and maintenance of mild or moderate hypothermia subsequently is effected at block 32 using the catheter 12 and/or pad 18, typically in the operating room or intensive care unit of a hospital, although in some hospitals the step at block 32 may begin while the patient is still in the emergency room or even while the patient is still in the ambulance.

The above three modalities of cooling—intravascular closed loop catheter, external pad/bladder, and cold saline bolus infusion—may be supported by a single housing.

Figure 3:
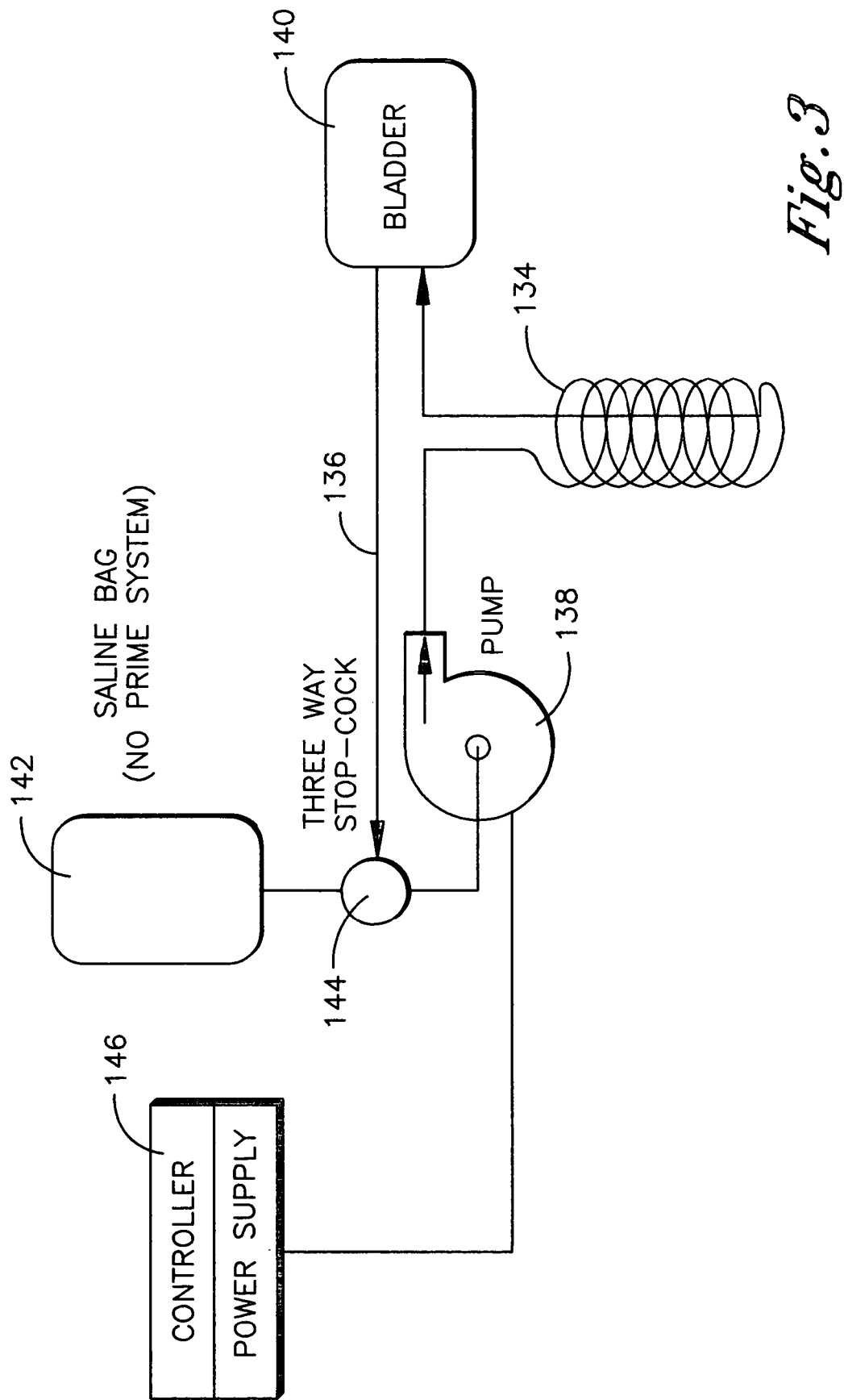
FIG. 3 is a diagram of a single heat exchange chassis system that supports both an external cooling bladder and an intravascular temperature control catheter.
Figure 3:
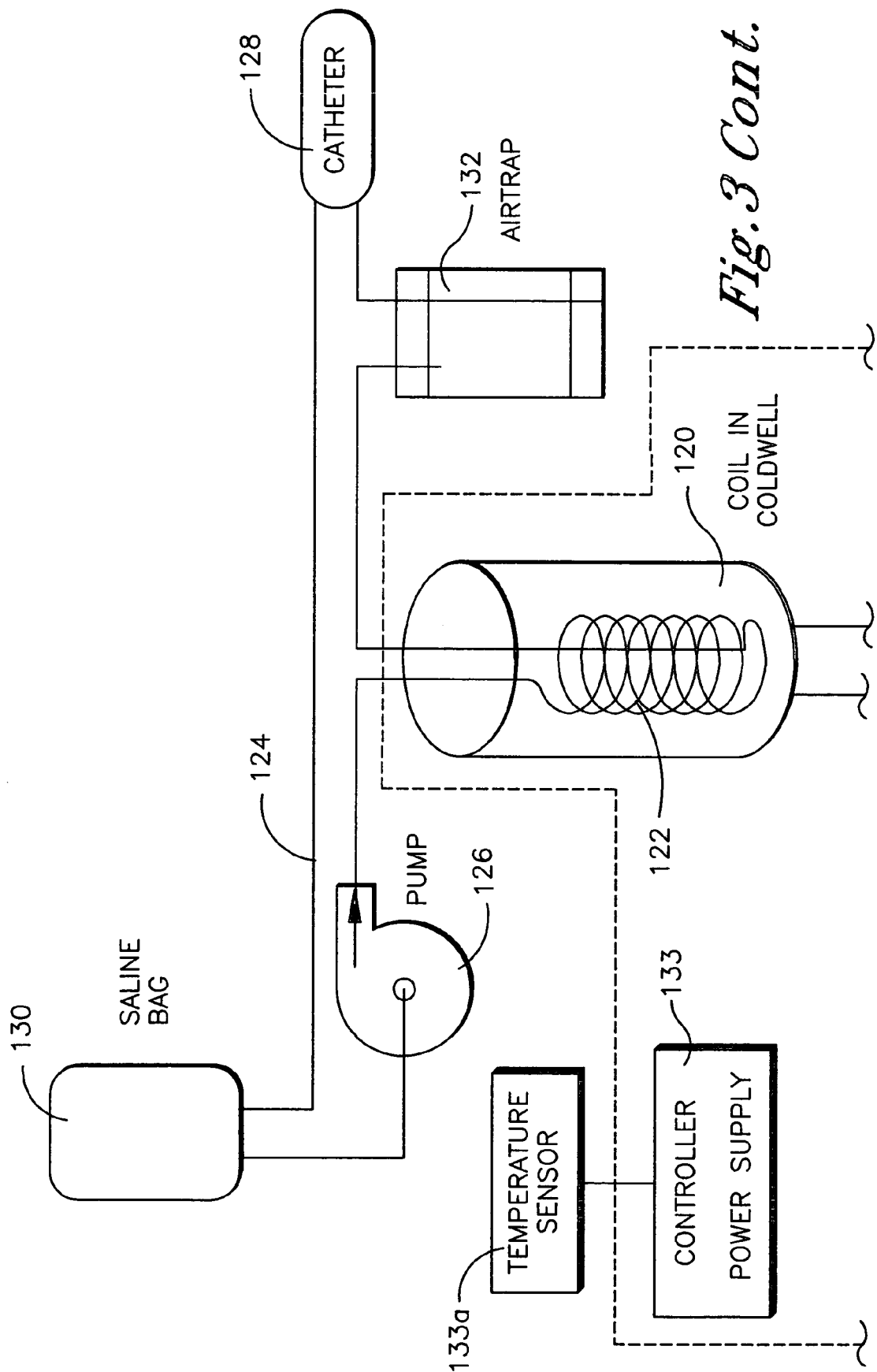
Figure 3:
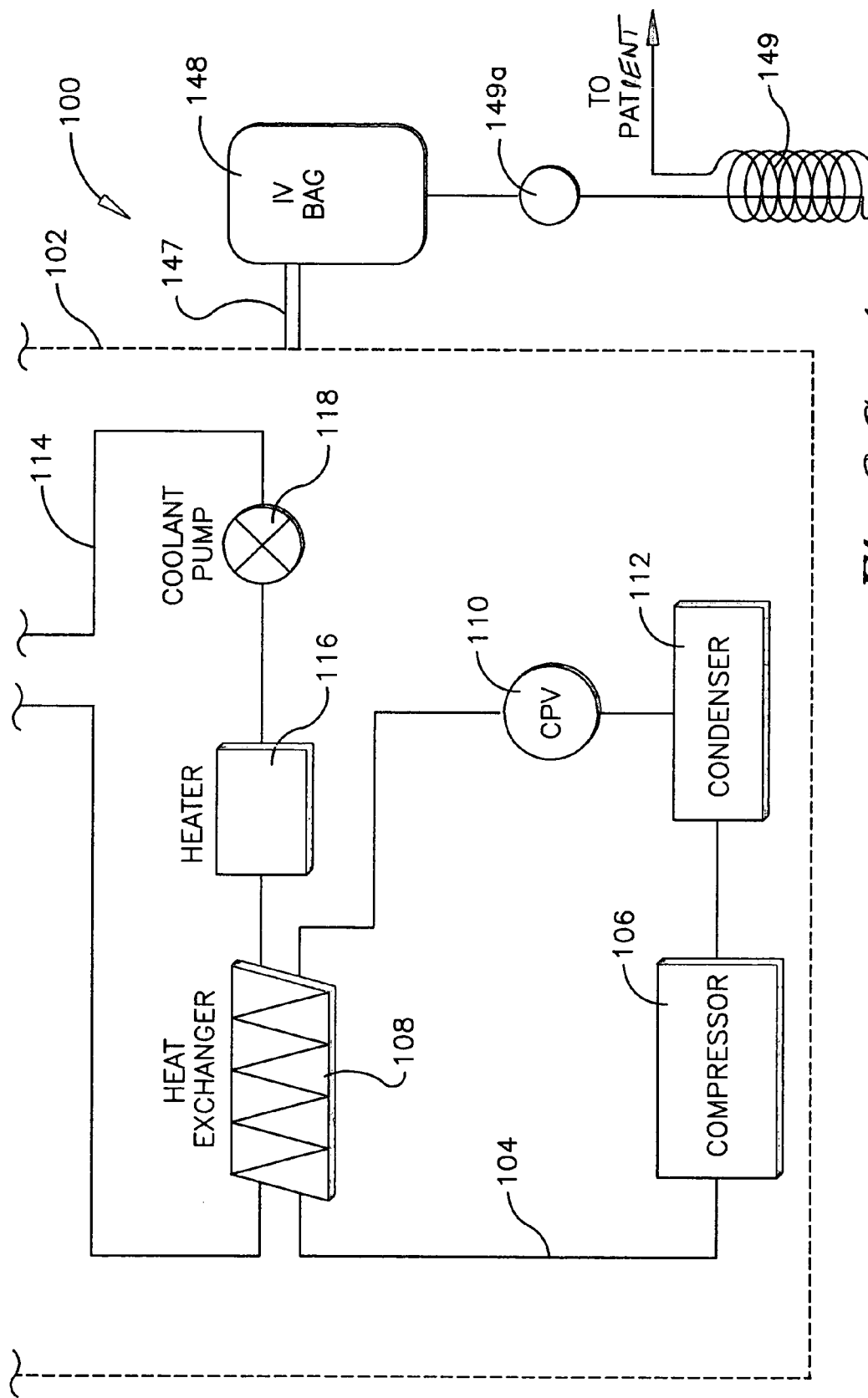

With greater specificity, FIG. 3 shows details of one non-limiting single-chassis heat exchange system, generally designated 100, which includes a single heat exchange system housing 102 holding all or portions of three fluid loops. Specifically, a refrigerant loop 104 exists in which refrigerant flows between a compressor 106 and at least one heat exchanger 108. Exiting the heat exchanger 108, the refrigerant passes through a CP valve 110 to a condenser 112, which condenses the refrigerant. The refrigerant loop 104 may be replaced by a thermoelectric cooling loop in which the fluid is air passing over and cooling a TEC element.

In the heat exchanger 108, the refrigerant expands to cool a coolant in a coolant loop 114, which is in thermal but not fluid contact with the refrigerant loop 104. The coolant may be water, propylene glycol, a mixture thereof, or other suitable coolant. Also included in the coolant loop 114 is a heater 116 for heating the coolant to, e.g., re-warm a patient, and a coolant pump 118 to circulate the coolant through the coolant loop 114. The coolant pump may be a magnetically-coupled non-displacement pump, or a positive displacement pump.

FIG. 3 shows that the coolant flows into a chamber defined by a coldwell 120, which may be the highest point in the system. A catheter fluid loop coil 122 may be disposed in the coldwell 120 in thermal but not in fluid contact with the coolant. The catheter fluid loop coil 122 defines part of a working fluid loop 124 through which a working fluid such as saline flows. The fluid in the working fluid loop 124 circulates, under the influence of a working fluid pump 126, which can be a peristaltic pump, through an intravascular heat exchange catheter 128 without exiting the catheter into the bloodstream. The working fluid exchanges heat with the coolant in the coldwell 120. A saline bag 130 may be provided in the working fluid loop 124 for priming purposes, and an air trap 132 may also be provided to prevent any air that might exist in the working fluid loop 124 from entering the catheter 128. The entire working fluid loop 124 may be provided as a standalone catheter start-up kit, with the catheter fluid loop coil 122 disposed by medical personnel in the coldwell 120 and with the catheter 128 then being advanced into the vasculature of a patient to exchange heat with the patient. Additional details of the non-limiting system 100 may be found in the present assignee's U.S. Pat. Nos. 6,146,411, 6,581,403, and 6,529,775, all of which are incorporated herein by reference, and in U.S. patent application Ser. No. 10/944,544, filed Sep. 17, 2004, also incorporated herein. The above patents further disclose non-limiting ways in which a controller/power supply 133 controls various of the components above to heat or cool the working fluid as necessary to achieve a user-set target temperature. A patient temperature sensor 133a can send a patient temperature signal to the controller 133 as shown. The sensor 133a may be any suitable sensor including, without limitation, a brain temperature tunnel (BTT) sensor to sense the temperature through thin peri-occular skin of a sinus, which represents the temperature of the brain.

Still referring to FIG. 3, in lieu of placing the catheter fluid loop coil 122 in the coldwell 120 and the catheter 128 in the patient, a bladder cooling loop coil 134, which is part of a bladder fluid loop 136, may be disposed in the coldwell 120. A bladder fluid pump 138, which can be a positive displacement pump, circulates working fluid, which could be tap water or saline or other appropriate fluid, through the loop 136. Included in the loop 136 is an externally-applied bladder 140 through which the working fluid flows to cool a patient. The bladder 140 may be any suitable cooling device such as a conformal pad or a mattress that is placed against the skin, including any of the devices referred to previously. An adhesive or non-adhesive hydrogel and/or a silver sulphur diazene cream or zinc paste may be disposed between the bladder and patient. Or, a skin conditioning hydrogel such as glycerol in sorbolene can be used. The bladder itself may be configured as the front of a shirt or trousers, i.e., with a trunk portion and two opposed limb portions that can drape over the patient. The surface of the bladder that faces away from the patient can be backed by a NASA foam that conforms to pressure caused by the weight of the patient to reduce the risk of bedsores.

A saline bag 142 may be provided in the loop 136 for priming. Also, a three-way stopcock 144 can be provided as shown to isolate the bag 142. The loop 136 may be controlled by a separate bladder controller/power supply 146, which may communicate with the controller 133 if desired.

An IV pole 147 may be mounted on the housing 102 and may support an IV bag 148, for infusing cold saline in the IV bag directly into the bloodstream of the patient as shown. A coil 149 may be provided in communication with the IV bag. The coil 149 may be disposed in the coldwell 120 to cool saline in coil, which can circulate under the influence of a pump 149a.

Figure 4:
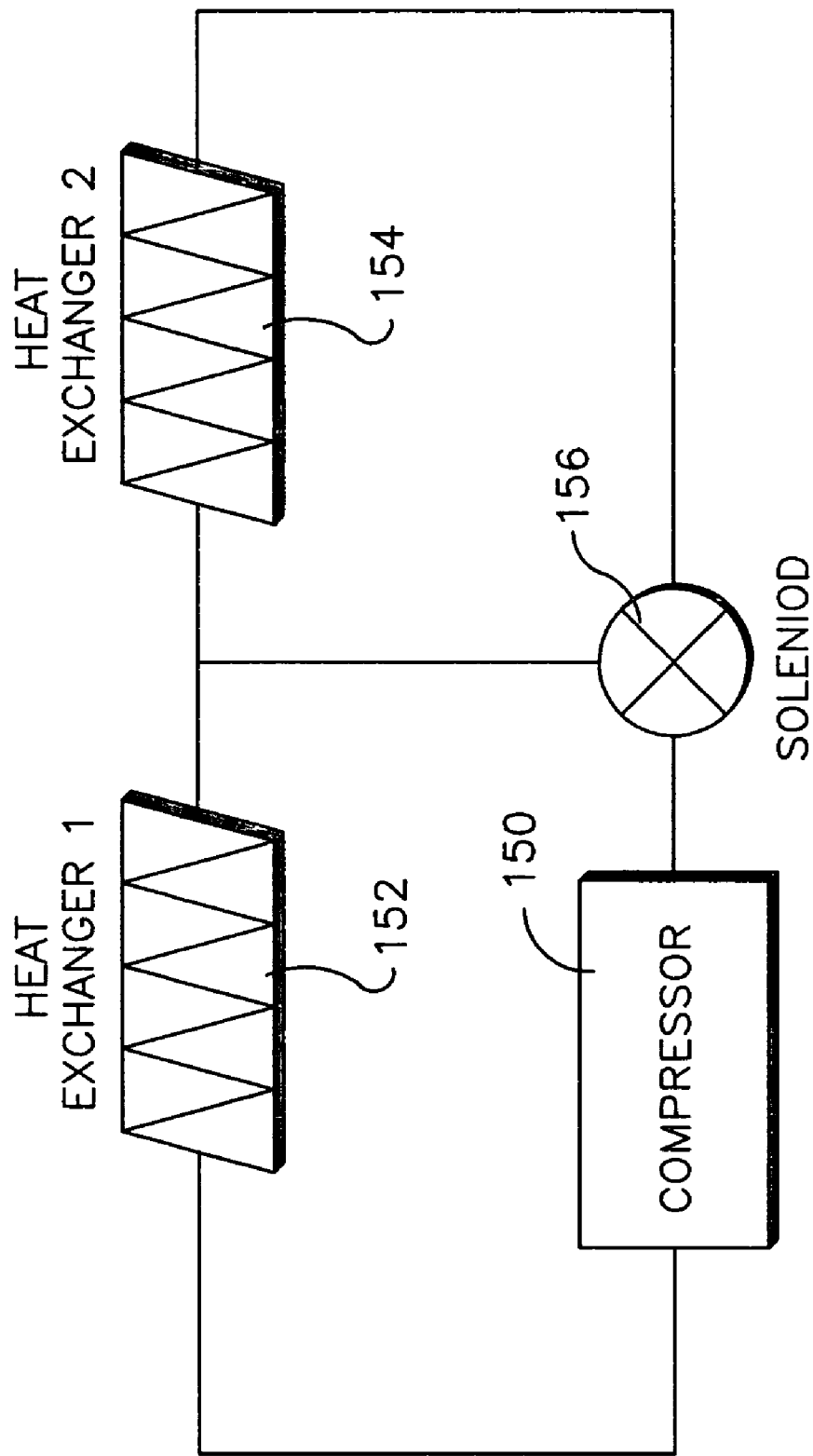
FIG. 4 is a schematic diagram showing that the heat exchange system can have two heat exchangers in parallel with one compressor.

FIG. 4 shows that for greater heat exchange power, a compressor 150 may circulate refrigerant through two heat exchangers 152, 154, either in parallel with each other or with one of the heat exchangers isolated by means of a computer-controlled solenoid valve 156. The arrangement shown in FIG. 4 could be used in lieu of the arrangements shown in the other figures herein.

FIG. 5 shows the coolant loop portion 200 of an alternate system 202, which in all essential respects is identical to the system 100 shown in FIG. 3 with the following exceptions. Coolant such as water may flow, under the influence of a coolant pump 204, through a heat exchanger 206 and a computer-controlled three-way valve 208, which either sends the coolant to a coldwell 210 to exchange heat with the coil of an intravascular catheter as described above, or to a bladder loop 212 that includes an external heat exchange bladder 214 as shown. A priming reservoir 216, which can be internal to the chassis of the system 202, may be provided for priming the bladder 214 with coolant, it being understood that in some embodiments the coldwell itself can be used for priming instead, in which case an additional three-way valve between the coldwell and first three-way valve 208 could be required for establishing the appropriate fluid flow control.

In any case, as shown in FIG. 5 the bladder 214 is connected to a supply line 218 and a return line 220, with the lines 218, 220 terminating in respective bladder fittings 222, 224 that engage respective system fittings 226, 228 on the chassis of the system 202. Preferably, the fittings are quick disconnect fittings that provide an indication of engagement and disengagement to the controller (not shown) of the system 202 for establishing the position of the three-way valve 208 for catheter or bladder operation as appropriate. Thus, in FIG. 5 the coolant loop supplies either the coldwell for exchanging heat with the working fluid circuit of the intravascular catheter, or it supplies the bladder directly.

It is undesirable that the heat exchanger freeze during, e.g., priming. Accordingly, when the system detects the bladder being connected, it can maintain system fluid temperatures above the freezing point. In any case, to avoid skin damage it is preferred that when the bladder is used the coolant temperature be maintained between four and forty two degrees Celsius.

Figure 6:
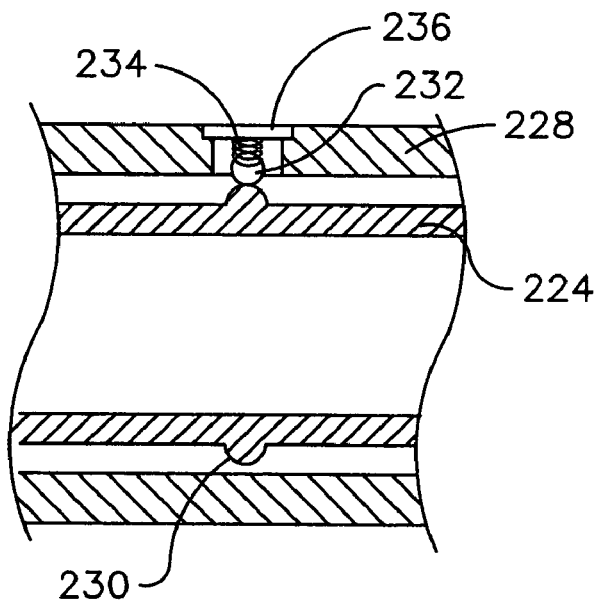
FIG. 6 is a cross-section of a non-limiting quick disconnect feature as would be seen along the line 6—6 in FIG. 5.

A non-limiting example of quick disconnect fittings (using 224, 228 as examples) is shown in FIG. 6. As shown, the bladder fitting 224 may be circumscribed by a collar 230, and as the bladder fitting 224 is advanced into the system fitting 228, the collar 230 deflects a ball 232 that is reciprocally disposed in the wall of the system fitting 228 and that is urged inwardly (toward the bladder fitting 224) as shown by a spring 234. As the ball 232 deflects, it actuates a sensing element 236 on the system fitting 228 to provide an "engaged" signal to the system controller, which can then reconfigure the user interface and/or control parameters used for establishing patient temperature. Or, the ball and spring can be omitted and the collar seat against the sensing element when the fittings are engaged, to actuate the sensing element. Other arrangements known in the art may be used. The sensing element 236 may be an electrical contact or other suitable element known in the art. It is to be understood that the catheter start-up kit shown in FIG. 3 may also be connected to the system using such fittings, so that in any of the embodiments herein, the controller "knows" which device or devices, catheter and/or bladder, is connected.

Figure 7:
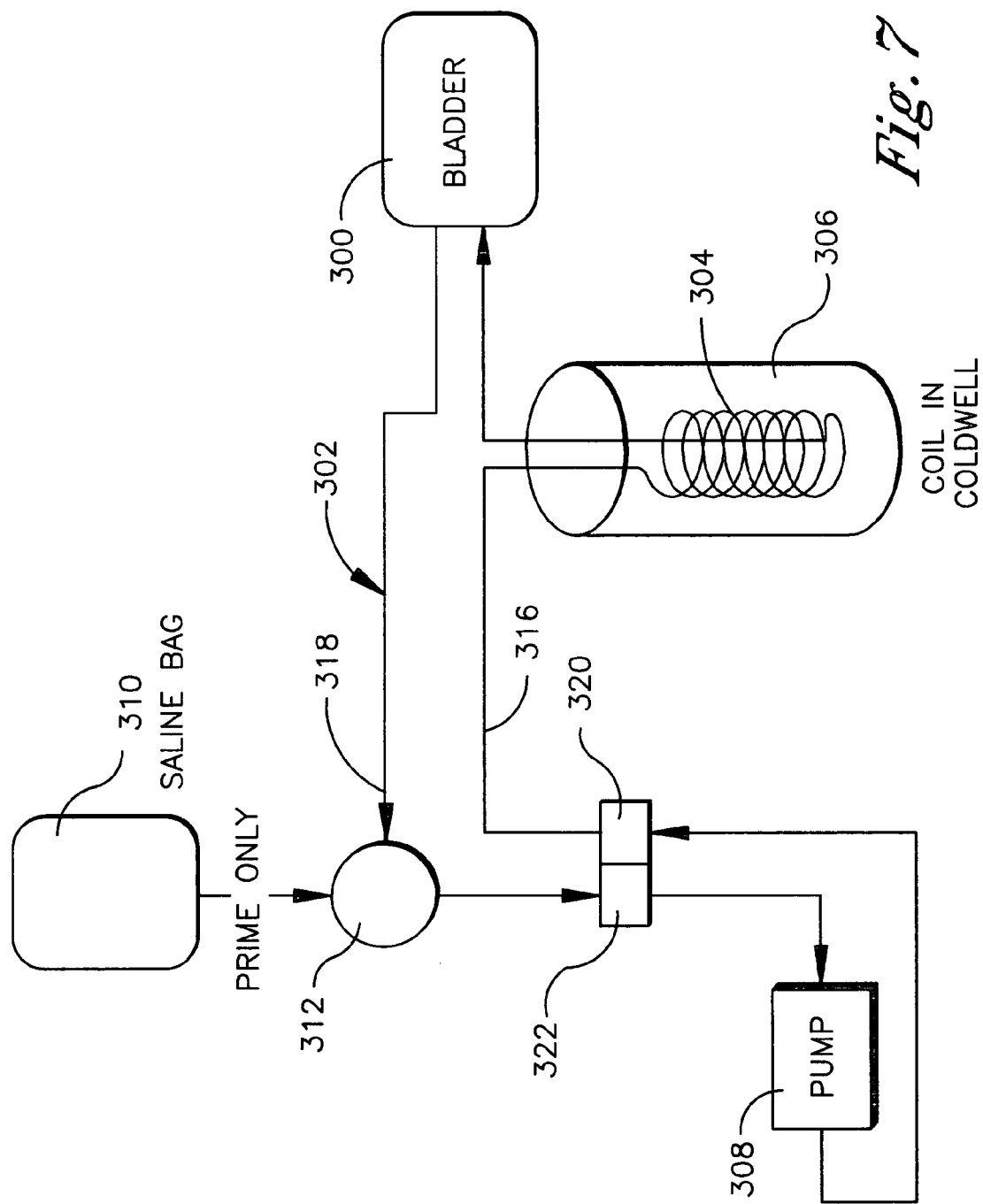
FIG. 7 is a schematic diagram of an alternate system.

FIGS. 7 and 8 show alternate embodiments in which a bladder 300 is part of a bladder working fluid loop 302 that includes a bladder coil 304 disposable in a bladder coldwell 306, it being understood that the catheter-related working fluid loop shown in FIG. 3 with separate catheter coldwell and catheter working fluid loop pump is also provided in a system that includes the refrigerant loop and working fluid loop shown in FIG. 3. In essence, in the systems of FIGS. 7 and 8 two separate working fluid loops are provided, one for the external cooling bladder and one for the intravascular catheter, with both loops being controlled by a common controller, e.g., the controller 303 shown in FIG. 3. In any case, a bladder working fluid loop pump 308 provides the motive force for circulating the working fluid. Either an external saline bag 310 (FIG. 7) can be provided for priming through a three-way stopcock 312, or a reservoir 314 (FIG. 8) that is internal to the system chassis can be provided. In both cases, a supply line 316 to the coil 304 and a return line 318 from the bladder 300 (or from the stopcock 312 when one is used as shown in FIG. 7) terminate in quick-disconnect fittings 320, 322 as shown, for operation as described above to alert the system controller to whether the bladder is connected. In the embodiments shown in FIGS. 7 and 8, since two separate working fluid loops are provided, both the catheter and the bladder can be simultaneously controlled by the controller to heat or cool a patient. Or, if simultaneous catheter/bladder use is not required, the bladder loop may not include its own coldwell and pump but rather can use a single coldwell that services either catheter and bladder.

While the particular SYSTEM AND METHOD FOR BRINGING HYPOTHERMIA RAPIDLY ONBOARD as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A system for controlling patient temperature, comprising:
   a closed loop heat exchange catheter configured for placement in the circulatory system of a patient to exchange heat with the blood of the patient;
   an external heat exchange bladder configured for exchanging heat with the skin of a patient; and
   a heat exchange system engageable with both the catheter and the bladder, wherein the heat exchange system includes at least one coolant loop having a coldwell, the catheter being associated with a catheter working fluid loop including a catheter coil disposable in the coldwell, the bladder being associated with a bladder working fluid loop including a bladder coil.

2. The system of claim 1, wherein the heat exchange system includes a housing holding at least one sensor sensing the fluid flow engagement of the heat exchange system with at least one of: the bladder, and the catheter, the sensor providing a signal to a controller in the housing.

3. The system of claim 1, comprising a controller receiving a patient temperature signal from a BTT sensor.

4. The system of claim 1, comprising at least one IV bag supported on a housing of the system for infusing cold saline through an IV line and directly into the bloodstream of a patient.

5. The system of claim 1, wherein the heat exchange system includes at least one coolant loop, the coolant loop configured for exchanging heat with a working fluid loop associated with the catheter, the coolant loop also being configured for fluid communication with the bladder.

6. The system of claim 1, wherein the heat exchange system includes at least one refrigerant loop including a compressor and at least one heat exchanger communicating with the compressor.

7. The system of claim 6, comprising two heat exchangers in fluid flow parallel with each other.

8. The system of claim 1, wherein both working fluid loops are associated with respective pumps.

9. The system of claim 8, wherein the heat exchange system includes an internal reservoir for priming the bladder.

10. The system of claim 1, wherein the heat exchange system simultaneously controls respective temperatures of respective fluids flowing through both the catheter and bladder.

11. A heat exchange system, comprising:
    a coolant loop;
    at least a first working fluid loop in thermal communication with the coolant loop;
    at least one intravascular heat exchange catheter associated with the first working fluid loop such that working fluid circulates through the heat exchange catheter without entering the patient's bloodstream when the catheter is positioned in the bloodstream; and
    at least one external heat exchange member configured for placement against a patient's skin to heat or cool the skin, the external heat exchange member being configured for heat transfer using the coolant loop.

12. The system of claim 11, wherein the external heat exchange member is associated with a second working fluid loop, the second working fluid loop exchanging heat with the coolant loop.

13. The system of claim 11, wherein the external heat exchange member is configured for connecting to the coolant loop to receive coolant therefrom.

14. The system of claim 11, wherein the coolant loop is embodied in a heat exchange system contained in a single housing and engageable with both the catheter and the external heat exchange member.

15. The system of claim 14, wherein the housing includes at least one sensor sensing the fluid flow engagement of the heat exchange system with at least one of: the external heat exchange member, and the catheter, the sensor providing a signal to a controller in the housing.

16. The system of claim 14, comprising a controller in the housing and receiving a patient temperature signal from a BTT sensor.

17. The system of claim 14, comprising at least one IV bag supported on the housing for infusing cold saline directly into the bloodstream of a patient.

18. The system of claim 14, wherein the heat exchange system simultaneously controls respective temperatures of respective fluids flowing through both the catheter and bladder.

19. A method for patient temperature control, comprising:

providing a heat exchange system;

engaging an intravascular heat exchange catheter with the system and with a patient to exchange heat with the patient; and engaging at least one bladder with the system and placing the bladder against the patient's skin to exchange heat with the patient.

* * * * *